US 11,837,333 B1

United States Patent
Shuang et al.

(10) Patent No.: US 11,837,333 B1
(45) Date of Patent: Dec. 5, 2023

(54) SIMULATION GUIDED INVERSE DESIGN FOR MATERIAL FORMULATIONS

(71) Applicant: Dow Global Technologies LLC, Midland, MI (US)

(72) Inventors: Bo Shuang, Missouri City, TX (US); Sukrit Mukhopadhyay, Midland, MI (US); Fabio Aguirre Vargas, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 18/085,336

(22) Filed: Dec. 20, 2022

(51) Int. Cl.
*G16C 20/30* (2019.01)
*G16C 20/70* (2019.01)
*G06N 5/022* (2023.01)

(52) U.S. Cl.
CPC ............. *G16C 20/30* (2019.02); *G06N 5/022* (2013.01); *G16C 20/70* (2019.02)

(58) Field of Classification Search
CPC ......... G16C 20/30; G16C 20/60; G16C 20/70
See application file for complete search history.

(56) References Cited

U.S. PATENT DOCUMENTS

| 8,655,633 | B2 | 2/2014 | Ibay |
| 10,647,981 | B1 * | 5/2020 | Luckey ............ C12N 15/1075 |
| 10,984,145 | B1 | 4/2021 | Hutchinson et al. |
| 11,537,898 | B2 | 12/2022 | Hegde et al. |

(Continued)

FOREIGN PATENT DOCUMENTS

| CN | 111611748 | 9/2020 |
| CN | 111800265 | 6/2021 |
| CN | 113127973 | 7/2021 |
| CN | 113450882 | 9/2021 |

(Continued)

OTHER PUBLICATIONS

Avery, "Predicting superhard materials via a machine learning informed evolutionary structure search", Condensed Matter, 2019, pp. 1-13.

(Continued)

*Primary Examiner* — Lam S Nguyen

(57) ABSTRACT

Methods include generating a hypothetical formulation library of chemical formulations, including generating hypothetical formulations by one or more of: (a) directed combinatorics including: selecting starter formulations from historical data; performing substitution of one or more formulation components in at least one component class; and assigning concentration ratios within ranges established by the historical data; and (2) constrained randomization including: preparing template formulations including one or more component classes based on historical data; performing randomized substitution of formulation components in each of the component classes of the template formulations; randomly assign concentration ratios to the formulation components within ranges established by one or more constraints to produce hypothetical formulations; create descriptors for the hypothetical formulations; compare descriptor outputs from the hypothetical formulations with the range of descriptor outputs from the historical data; and remove duplicate and outlier formulations; and collecting the hypothetical formulations into the hypothetical formulation library.

10 Claims, 5 Drawing Sheets

(56) References Cited

U.S. PATENT DOCUMENTS

| | | | |
|---|---|---|---|
| 2002/0152057 A1* | 10/2002 | Wang | G16C 20/62 |
| | | | 703/6 |
| 2003/0149933 A1* | 8/2003 | Falcioni | G16C 20/62 |
| | | | 506/13 |
| 2019/0057313 A1 | 2/2019 | Hirshman et al. | |
| 2021/0110890 A1* | 4/2021 | Agarwal | G16C 20/64 |
| 2021/0280276 A1 | 9/2021 | Gupta et al. | |
| 2021/0397949 A1 | 12/2021 | Wang et al. | |

FOREIGN PATENT DOCUMENTS

| | | |
|---|---|---|
| CN | 113312807 | 11/2021 |
| JP | 2020030680 | 2/2020 |
| KR | 2288059 | 8/2021 |

OTHER PUBLICATIONS

Chehade, "Accelerating the Discovery of New DP Steel Using Machine Learning-Based Multiscale Materials Simulations", Metallurgical and Materials Transactions A: Physical Metallurgy and Materials Science, 2020, vol. 51, iss. 6, pp. 3268-3279.

Guo, "Artifical intelligence and machine learning in design of mechanical materials", Materials Horizons, 2021, vol. 8, iss. 4, pp. 1153-1172.

Hashemi, "A supervised machine learning approach for accelerating the design of particulate composites: Application to thermal conductivity", Computational Materials Science, 2021, vol. 197, iss. 110664.

Hashimoto, "Optimization of Work Function via Bayesian Machine Learning Combined with First-Principles Calculation", Journal of Physical Chemistry C, 2020, vol. 124, iss. 18, pp. 9958-9970.

Kim, "Polymer design using genetic algorithm and machine learning", 2021, vol. 186, iss. 110067.

Osorio, "From soltuion to device: processing approaches to boost the photovoltaic performance of organic solar cells", Master of Science.

* cited by examiner

200

202
Separate formulation components from historical data into component classes to generate at least one template formulation.

204
Perform randomized substitution of formulation components each of the component classes of the formulation templates

206
randomly assign concentration ratios to the formulation components within ranges established by one or more constraints to produce one or more hypothetical formulations

208
Generate one or more descriptors for the obtained hypothetical formulations.

210
Compare descriptors with values for associated historical data. Remove duplicate and outlier formulations identified to obtain hypothetical formulation data set.

SIMULATION GUIDED INVERSE DESIGN FOR MATERIAL FORMULATIONS

FIELD

Embodiments relate to computer-based methods for generating prospective chemical formulations given an input of one or more desired target product properties. Methods may also include validating a prospective formulation and modifying a chemical process accordingly.

INTRODUCTION

The design of chemical formulations across industries often involves combining various chemical components to generate a product having one or more target product properties through labor intensive methodologies that can involve serial and/or parallel high throughput experimentation. However, as the scale and complexity of the chemical formulations increase, the number of combinations and experiments needed to map the chemical parameter space increases exponentially. This has led to the development of computer-based approaches that utilize Machine Learning models trained using volumes of historical formulation data that generate predicted target properties from an input prospective formulation.

To gain full utility of such Machine Learning modeling approaches, users must be able to design and customize prospective formulations that can then be surveyed as meeting desired target properties (forward model). Modeling approaches to survey prospective formulations with the desired one or more target product properties requires generating a series of prospective formulations by software trained using machine learning methodologies and search them (inverse model). The prospective formulations may then be validated through various experiments to verify that all design criteria are satisfied. However, previous modeling approaches require training machine learning models using large volumes of historical data, are often unconstrained by field-specific and empirical knowledge from the field, and low numbers of potential formulations.

SUMMARY

Methods may include generating a hypothetical formulation library of chemical formulations, comprising generating hypothetical formulations by one or more of: (a) directed combinatorics, comprising: selecting one or more starter formulations from historical data; performing substitution of one or more formulation components in at least one component class for each of the starter formulations; and assigning concentration ratios to the formulation components within ranges established by the historical data; and (b) constrained randomization, comprising: preparing one or more template formulations including one or more component classes based on historical data; perform randomized substitution of formulation components for each of the component classes of the template formulations; randomly assign concentration ratios to the formulation components within ranges established by one or more constraints to produce one or more hypothetical formulations; create one or more descriptors for the hypothetical formulations; compare descriptor outputs from the hypothetical formulations with the range of descriptor outputs from the historical data; and remove duplicate and outlier formulations; and collecting the hypothetical formulations into the hypothetical formulation library.

BRIEF DESCRIPTION OF THE DRAWINGS

FIG. 2 is a flow diagram illustrating a method of using constrained randomization to develop one or more prospective chemical formulations.

DETAILED DESCRIPTION

Figure 1:
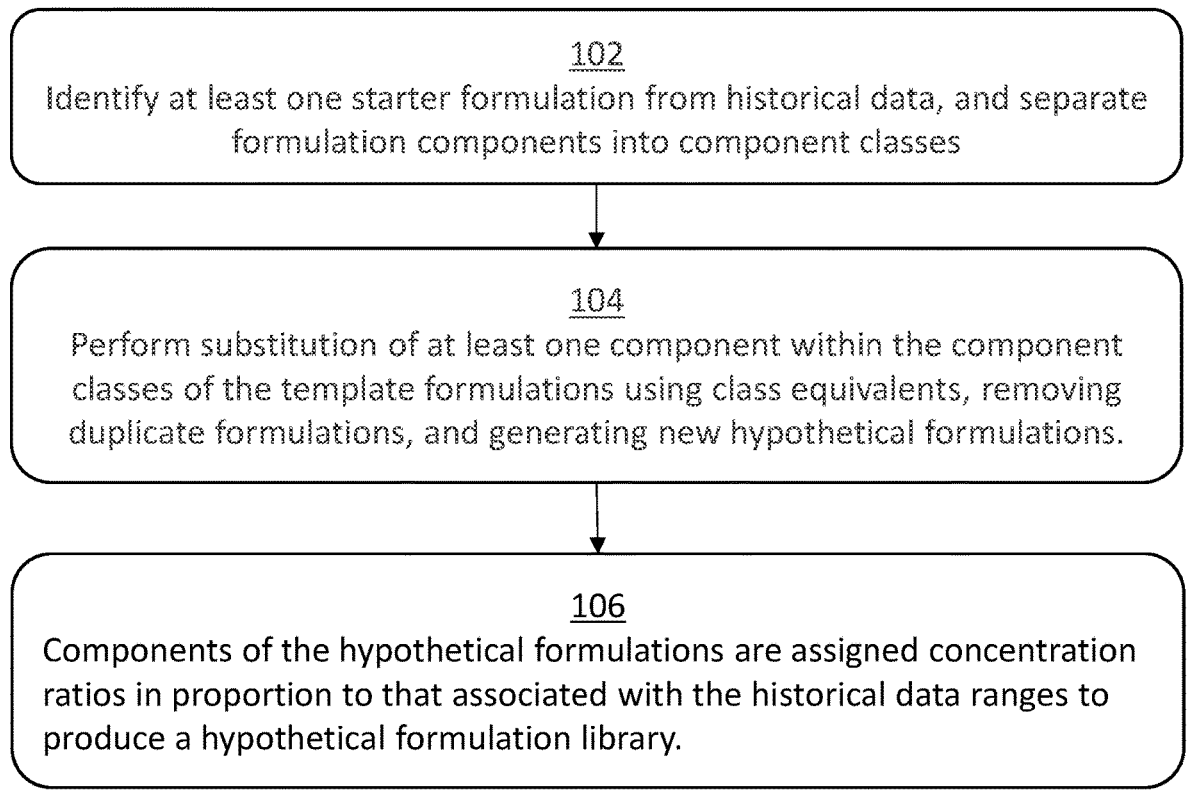
FIG. 1 is a flow diagram illustrating a method of using directed combinatorics to develop one or more prospective chemical formulations.

Methods disclosed herein enable the generation of hypothetical formulation libraries, which are generated using (1) directed combinatorics, and (2) constrained randomization, which may be combined with machine learning-based validation techniques for optimization prior to experimental validation and application. In some cases, methods may include inverse design approaches to generating a hypothetical formulation library containing one or more prospective chemical formulations derived from input of one or more desired target product properties.

As used herein, "machine learning modules" refers to a software package that may include one or more machine learning models, which are trained, or capable of being trained, to estimate a target product property given an input, such as a training, testing or experimental data set.

As used herein, "formulations" refers to compositions of components (e.g., polymer compositions, reactant mixtures, blends, etc.) for particular applications.

As used herein, "component" refers to chemical species and/or chemical classifications (e.g., including but not limited to monomers, prepolymers, chemical species containing none, one or more reactive groups, catalysts, etc.).

As used herein, "process conditions" (e.g., atmospheric pressure, variable pressure foaming, relative humidity, overpacking percentage, etc.) refers to an expression describing the process conditions affecting the properties.

As used herein, "descriptor" (e.g., monomer mw, water content, catalytic activity, polymer chain entanglement, etc.) refers to an expression describing a correlation within a chemical system that can provide additional information and/or generalizations regarding system behaviors Descriptors herein may be calculated from component information and concentration using various physics-based approaches and models target product properties.

As used herein, "target product property" refers to a property associated with a unique chemical formulation (e.g., chemo-rheology, foam density, hardness, modulus, etc.) that is selected based on desired user input for a given product application. Target product properties may be obtained from historical data and used to train a machine learning module. When trained, machine learning modules may then generate predicted target product properties from an input of a prospective chemical formulation. In some cases, the determination of multiple target product properties by a machine learning module may be done simultaneously, in series, in parallel, or any other suitable subcombination.

As used herein, "variable parameter" refers to a feature of a machine learning module and/or model that can be varied during training (e.g., chemical species and/or class, concentration, descriptor value, etc.).

Prior approaches include the generation of arbitrary compositions according to a methodology that generates rules among a selection of components according to combinatorial principles and component functions. The disadvantages of standard combinatorial approaches are that the large number of potential combinations strain computational resources and time, and the virtually generated compositions are unrepresentative and have limited correspondence with historical data.

Methods of generating hypothetical formulation libraries may include production of data sets having controllable size, which may be combined with a user interface retrieval of hypothetical formula libraries, which may be near-instantaneous in some cases. Two approaches to hypothetical data library generation include (1) directed combinatoric in which at least one formulation component is modified at a time from historical data; and (2) constrained randomization that utilize constraints and descriptors built from historical data to limit the scope of randomization such that the prospective formulations remain within an range that corresponds to historical data Hypothetical formulation libraries obtained by the methods disclosed herein may be processed through a machine learning module trained on historical data (and/or hypothetical data) and the targeted property is calculated for a hypothetical formulation library. Methods disclosed herein may also utilize inverse methodologies in which a hypothetical formulation library is generated, input into a machine learning models to predict one or more target product properties ("forward model"). These predictions can be used to refine the hypothetical formulation library to generate a subset of prospective chemical formulations that meet the desired requirements for target product formulations ("inverse model"). Predicted formulation properties may also be correlated with the prospective formulations and stored as a library and/or indexed for access.

Prospective formulation libraries may be generated by directed combinatorics in which a hypothetical library is generated from historical data sets. In general, directed combinatorics may be useful in cases where starter formulations are known and accompanied by historical data. With respect to FIG. 1, a methodology for generating a library of hypothetical formulations 100 using directed combinatorics is shown. At 102, at least one starter formulation is identified from historical data, and formulation components are separated into component classes. Component class selection is dependent on specific application, which may be defined by historical data from historical data and/or general knowledge. In some cases, classes may be constructed based on existing types of raw materials, or subdivided into classes by chemical type. For example, chemical formulation components for a polyurethane foam may be divided into classes for polyol, isocyanate, catalysts, surfactants, blowing agents, additives, and the like.

At 104, starter formulations are selected form the historical data set and random substitutions are made for at least one component within the component classes of the starter formulations using class equivalents, removing duplicate formulations, and generating new hypothetical formulations. For example, if a starter formulation uses components selected from classes a+b+c, hypothetical formulations may include a+b+d, a+e+c, f+b+c, etc. (where alternate letters represent functional class equivalents). In some cases, combinatorics may also substitute components into one or more classes, such as a+d+e, f+d+c, f+b+c, etc.

At 106, components of the hypothetical formulations are assigned concentration ratios in proportion to that associated with the historical data ranges to produce a hypothetical formulation library. In some cases, methods may also include varying the weight amount/ratio extend beyond the historical values by some amount, such as more or less than 5%, 10%, 15%, and the like.

Hypothetical formulation libraries may also be generated by constrained randomization in which one or more template formulations are extracted from historical data. Constrained randomization to generate hypothetical libraries may be favored in some cases where historical data is limited and parameter space is not well mapped (sparse data sets, for example).

With particular respect to FIG. 2, a methodology for generating a library of hypothetical formulations using constrained randomization 200 is shown. At 202, one or more template formulations are generated containing one or more component classes based on historical data and/or general field knowledge. Template formulations may be generated through the establishment of component classes based on defined chemical identities or function (e.g., polyols, isocyanates, catalysts, silicones, etc.), as described above for starter formulations.

At 204, template formulations are populated by randomized substitution of formulation components into each of the component classes. In some cases, randomization may be limited by the number of equivalents placed into each class according to the defined template formulation. For example, a template formulation for a polyurethane that contains a mixture of two polyols, may be randomized by substituting the two equivalent polyols, respectively, while not including or removing polyols. Randomization may also include linear combinations of multiple classes. In another example, randomization may involve linear combinations of component classes, such as the case in which the total amount of components in the classes for polyols and isocyanate are equal to 4, combinations may include 1 polyol and 3 isocyanates, 3 polyol and 1 isocyanates, 2 polyol and 2 isocyanates, etc.

At 206, concentration ratios are randomly assigned to the formulation components of the hypothetical formulations within ranges established by one or more constraints. Constraints may enhance the expected accuracy of hypothetical formulations based on historical data, while also limiting bandwidth consumption attributed to determination of target properties that lie outside of the ranges of the historical data and that are likely to have high error rates and low relevance.

Constraints may be created from one or more of concentration ranges, physical variables (e.g., molecular weight, functionality, polydispersity, ionic charge, and the like), and physics-based descriptors. In some cases, hypothetical formulations may be generated that remain within a 10% range of a selected constraint. For example, if the averaged molecular weight of a polyol component is between 1000 to 10000, randomized hypothetical formulations may be constrained to those formulations having averaged molecular weight within 900 to 11000. In another example, if a component is present in experimental data as a percent by weight (wt %) in a range of 5 wt % to 15%, a library of hypothetical formulations can be generated by restricting the wt % values within that range. Other examples of filters may include molecular weights, particle size, polarity, ionic strength, and the like. In some cases, component values may be extrapolated outside of the historical range by a specified value (e.g., 5%, 10%, and the like).

In some cases, randomly assigning concentration ratios to the formulation components includes selecting from among concentration ratios that are within 10% of the historical range for the given formulation component.

At 208, one or more descriptors are generated for the hypothetical formulations to determine key feature descriptors of interest. Descriptors for the hypothetical formulations may be generated by converting component physical properties and concentrations (e.g., wt %) to descriptors (e.g., OH-number, NCO, functionality, etc.) using suitable physics-based models/tools known in the art. Descriptors disclosed herein are computed from the properties of the individual components in the formulation, such as by using a physics model suited for the particular chemical application (e.g., polyurethane compositions). Descriptors may contain data regarding formulation components, component concentrations and ratios, such as ratios of polyurethane reactants (e.g., the ratio of the isocyanate component and polyol component), product generating reactions among components, and properties result from various chemical interactions (e.g., functionality for isocyanates or reactive species, crosslinking, blowing agent reactivity). Suitable descriptors also include those detailing mechanical properties, such as vapor heat capacity, foam density, Young's modulus, rheology properties, heat transfer properties, and the like.

At 210, key feature descriptors or linear/non-linear combinations of key feature descriptors are used to compare hypothetical formulations with corresponding expected descriptor values from historical data. Duplicate hypothetical formulations and outlier formulations outside the expected descriptor values are removed and the remaining formulations constitute the hypothetical formulation library. In some cases, outlier formulations may be defined as those in which a selected descriptor varies by more than 5%, 10%, or 15% with respect to the historical range for the descriptor.

Hypothetical formulation libraries may be input into a machine learning module to determine one or more predicted target product properties, including prediction intervals. Machine learning modules may include any suitable machine learning model trained to determine one or more target product properties. Suitable machine learning modules may include artificial neural networks such as deep neural networks (DNNs), symbolic regression, recurrent neural networks (RNNs) that include long short-term memory (LSTM) networks or Gated Recurrent Unit (GRU) networks, decision trees, random forests, boosted trees such as gradient boosted trees (XGBoost), linear regression, partial least squares regression, support vector machines, multilayer perceptron (MLP), autoencoders (e.g., denoising autoencoders such as stacked denoising autoencoders), Bayesian networks, support vector machines (SVMs), hidden Markov models (HMNIs), and the like. Commercially available software packages may include JMP software, Microsoft AzureML, SAP data analysis tools, soft independent modeling by class analogy (SIMCA) by Sartorius, and the like.

Machine learning architectures may also utilize deep learning in which a neural network is generated with multiple layers. These layers extract successively higher order features from a training data set. For chemical formulations, examples of layers containing lower order features may include general classifications of component type, while layers including higher order features in the network may include details dependent on functional groups, ionization state, charge, and the like.

Figure 3:
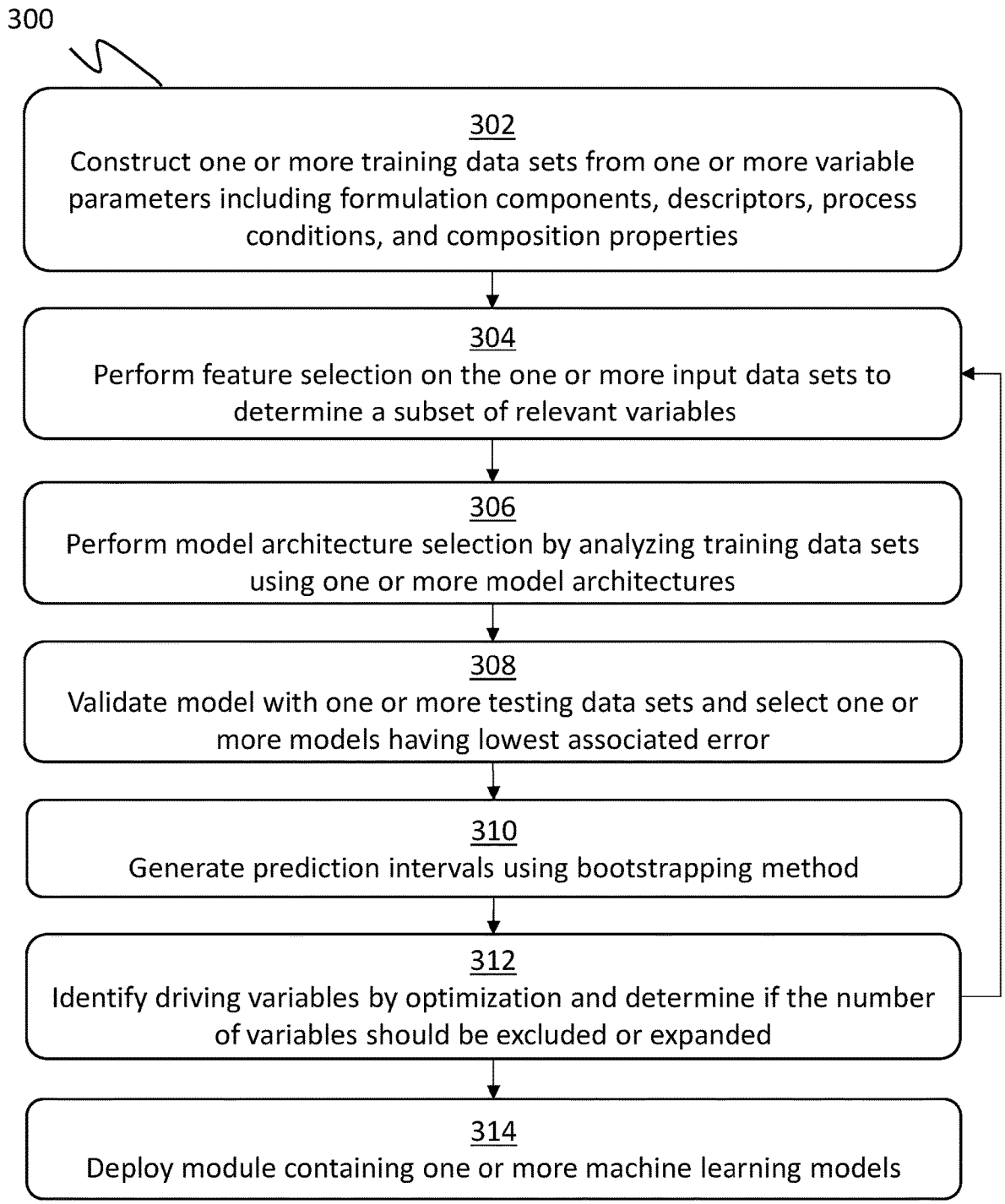
FIG. 3 is a flow diagram illustrating a method of training a machine learning module to estimate one or more target product properties for a prospective chemical formulation.

With particular respect to FIG. 3, machine learning modules disclosed herein may be trained using a training set composed of historical data and/or hypothetical data for a given chemical application (e.g., polyurethane foams). At 302, one or more training data sets are constructed from one or more variable parameters including formulation components, descriptors, process conditions, and composition properties.

Training data sets may also include one or more descriptors generated by converting component physical properties and concentrations (e.g., wt %) to descriptors (e.g., OH-number, NCO, functionality, etc.) using suitable physics-based models/tools known in the art. Descriptors disclosed herein are computed from the properties of the individual components in the formulation, such as by using a physics model suited for the particular chemical application (e.g., polyurethane compositions). Descriptors may contain data regarding formulation components, component concentrations and ratios, such as ratios of polyurethane reactants (e.g., the ratio of the isocyanate component and polyol component), product generating reactions among components, and properties result from various chemical interactions (e.g., functionality for isocyanates or reactive species, crosslinking, blowing agent reactivity). Suitable descriptors also include those detailing mechanical properties, such as vapor heat capacity, foam density, Young's modulus, rheology properties, heat transfer properties, and the like.

At 304, feature selection is performed on the training data set constructed in 302. During feature selection, a subset of the variable parameters identified in the training set are identified as "driving" variables affecting the targeted formulation property. Feature selection may then involve the exclusion of irrelevant, noisy, and redundant features from the training data set.

Feature selection techniques may include one or more of descriptor feature selection; removing constraining features; correlation testing methods such as Pearson, Spearman, Kendall, and the like; analysis of variance (ANOVA) univariate testing; mean absolute different testing; L1 or Least absolute shrinkage and selection operator (Lasso) regularization; multivariate analysis (baseline); and the like.

At 306, machine learning model architectures are surveyed by training one or more machine learning models with the driving variables established from 304 as input. The generated machine learning models from the surveyed architectures are then compared and rated for accuracy, which is then used to select one or more model architectures used in subsequent stages. For example, a machine learning module may output one or more predicated performance properties from a prospective chemical formulation. In some cases, more than one trained machine learning model may be combined into a machine learning module, where the output is the result of constituent machine learning model having higher accuracy for the selected target product property and/or is the result of averaging the output of one or more machine learning models.

At 308, the method further includes training and validating multiple models with a testing data set containing the variable data and target product property data, and then selecting an appropriate model based on desired model criteria such as best fit according to error calculation techniques such as $R^2$, mean associated percent error (MAPE), root mean squared error (RMSE), and the like. The testing data set may contain chemical formulation information and descriptor information that is similar in structure to the training data set, however, it usually contains sample information that is minimally duplicative to the training data in order to provide an adequate test of the ability of the machine learning module to handle new information, as opposed to storage and retrieval of the training data set values.

Underfitting is a scenario where a model cannot capture the relationship between the input and output variables. In the case of $R^2$-based methods, the underfitted models tend to have undesirably low training $R^2$. The training $R^2$ threshold may be set at a desired accuracy to filter out underfit models, such as greater than 0.70, 0.85, 0.88, or 0.9. Further, overfit models may occur in which the model is too closely aligned to the training data, and the learned representation cannot predict the validation data accurately. In some cases, error calculation techniques may also be used to select for generalizable models while filtering out overfitted models. For example, validation percentage RMSE threshold of less than 40%, 35%, or 30% may be used to predict target product properties.

In some cases, parameters for the model are optimized by minimizing the mean squared error (MSE) between the actual value $y_i$ and the predicted value $\hat{y}_i$, as shown in equation (I) below:

$$MSE = \frac{1}{n}\sum_{i=1}^{n}(y_i - \hat{y}_i)^2 \quad \text{(I)}$$

where n is the total number of data points, $y_i$ is the actual value of the target product property measured, i is the sample data point, and $\hat{y}_i$ is the model predicted value of the target product property.

MSE is a metric used to measure the average of the squares of the difference between the predicted values and the actual values. RMSE means root mean squared error that is a metric to measure the difference between the predicted values and the actual values. Percentage RMSE is the square root of MSE normalized by the population mean to a dimensionless number expressed as a percentage. The percentage RMSE can be calculated as below:

$$\text{percentage } RMSE = \frac{\sqrt{\sum_i^n \frac{(\hat{y}_i - y_i)^2}{n}}}{\overline{y}_i} \times 100 \quad \text{(II)}$$

where n, $y_i$, i and $\hat{y}_i$ are as defined above in equation (I) above, and $\overline{y}_i$ is the mean value for the target product property measured. The lower the percentage RMSE, the better the model fits a dataset.

$R^2$ means the coefficient of discrimination, which is a commonly used performance metric for regression that calculates the proportion of variance explained by a regression model. $R^2$ normally ranges from 0 to 1 and can be calculated according to equation (III) below:

$$R^2 = 1 - \frac{\sum_i(y_i - \hat{y}_i)^2}{\sum_i(y_i - \overline{y}_i)} \quad \text{(III)}$$

where $y_i$, i and $\hat{y}_i$ are as defined above in equation (I) above, and $\overline{y}_i$ is the mean value. The higher the $R^2$, the better the model fits a dataset.

In one embodiment, the method can provide predictions for target product properties of a chemical composition or product, as indicated by "training $R^2$>0.70" as calculated according to the equation (III) above, and test percentage RMSE less than 30% (<30%) as calculated according to the equation (II) above. In addition, validation percentage RMSE is <30% as calculated according to the equation (II) above. "Training $R^2$" refers to $R^2$ for the training dataset, "validation percentage RMSE" refers to the percentage RMSE for the validation dataset, and "test percentage RMSE" refers to the percentage RMSE for the test dataset.

At 310, prediction intervals are generated for the created models using bootstrapping (bagging) or ensembling methodologies to provide a measure of the probable error for target product property predictions. For example, prediction intervals may be represented as range of variance around the associated mean value. During bootstrapping, samples are drawn from the training data and input into a model, and the results are combined by averaging for regression and simple voting for classification, to obtain the overall prediction.

At 312, model optimization is used to identify driving variables to determine whether the obtained model accuracy is increased by removing or adding additional variables. Optimization methods may evaluate how significant each selected variable is in determining the prediction of the model outputs. The subset of variable having the greatest impact on model accuracy can then be used to determine if training process 300 is complete (e.g., prediction accuracy acceptable), or should be reiterated by repeating 304 to 312. In some cases, iterations may be repeated multiple times such as 2 to 3 or more.

Optimization methods may evaluate the selected variables on the target product properties output from the models and processed using interpreting and explanatory software, such as SHapley Additive ex-Planation (SHAP), Local Interpretable Model-Agnostic Explanations (LIME), and the like. For example, SHAP analysis assigns each input variable an importance value for a particular prediction by comparing a model's output with and without a specific variable. SHAP values are then computed using a sum that represents the impact of each input variable added to the model averaged over all possible orderings of variable being introduced. Positive SHAP values indicate that higher feature values lead, on average, to higher predicted values, while negative SHAP values indicate that lower feature values lead, on average, to lower predicted values.

At 314, the optimized and trained machine learning module is deployed and used to generate predicted target product properties for a prospective formulation.

Figure 4:
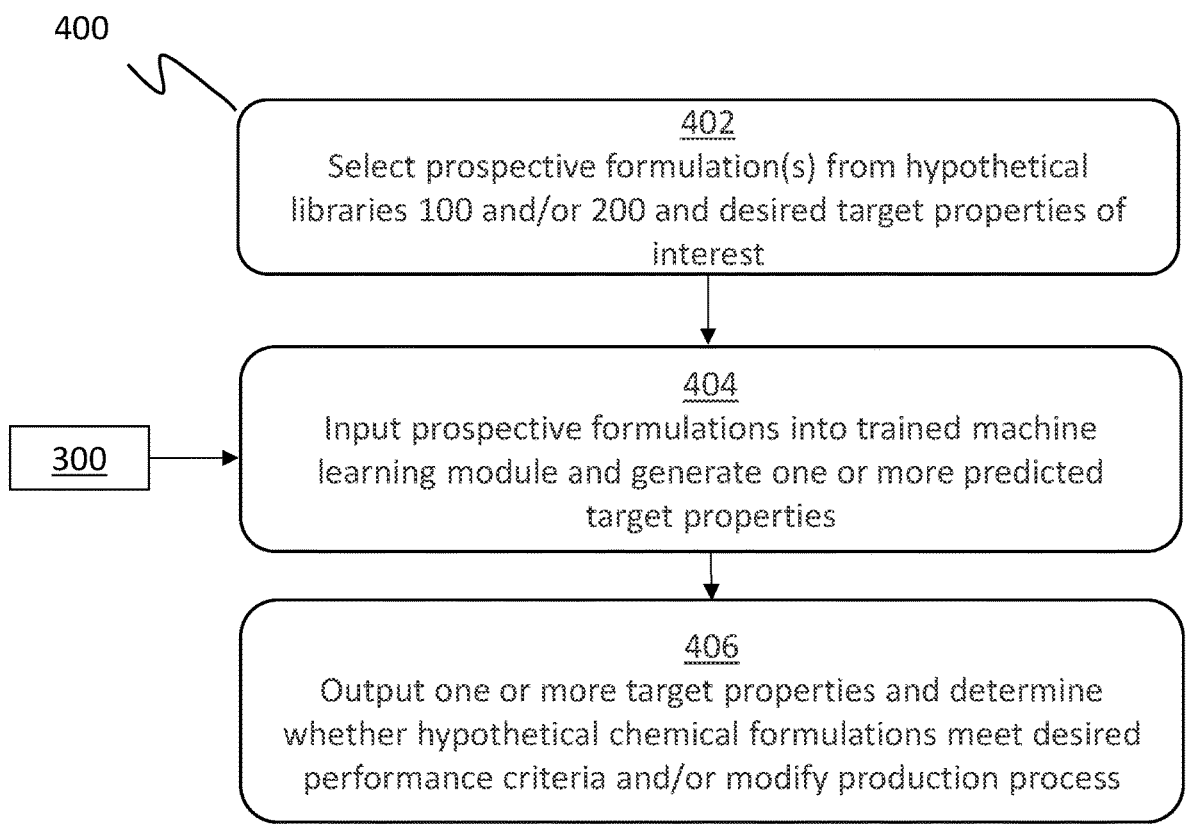
FIG. 4 is a flow diagram illustrating a method of predicting one or more target product properties from one or more prospective chemical formulations developed by directed combinatorics and/or constrained randomization.

With respect to FIG. 4, Hypothetical formulations are processed through a machine learning module trained on historical data and the targeted property is calculated for the hypothetical formulation set. The solved hypothetical formulation set is then stored as a searchable database (accessible online, for example).

Following training of the machine learning module, one or more prospective chemical formulations are input into a machine learning module to produce one or more predicted target product properties. Methods disclosed herein produce prospective formulations that are closely fit to the experimental/training data.

FIG. 4 illustrates a method of using a trained machine learning module to generate one or more target product properties from a prospective formulation. 402, select prospective formulation(s) from hypothetical libraries based on historical data using directed combinatoric (100) or constrained randomization (200) are selected and input into a trained machine learning module to calculate one or more predicted target product properties at 404.

At 404, hypothetical formulations to the ML models to predict the properties of the hypothetical formulations. This completes the new hypothetical formulations generation process.

At 406, one or more predicted target product properties are generated as an output. The predicted properties may be used to determine whether prospective chemical formulation meets desired performance criteria, or whether further modifications to the formulation or article production process should be made. Target product property output may also be used to evaluate a produced product or article, allowing an operator to accept or reject a product produced from the prospective chemical formulation and/or chemical process. Modifications may include inclusion or removal of chemical components or various additives, modifying process parameters such as reaction temperatures, concentrations, reactor design, and the like. For example, predicted target product properties may be include adjusting a polyurethane-forming reaction to include more or less catalyst to control target product properties such as density and hardness.

In some cases a user may utilize an interface that enable the selection of formulation components, respective concentrations, and target product property (or properties) of interest. Once the desired criteria are input, the machine learning module provides a prediction of the target product property. The target product property generated may then be used to inform one or more of whether the prospective formulation should be further adjusted to meet the desired target product property, whether a process for generating a formulation or reaction product should be adjusted, and whether a produced product meets the expected criterion. The disclosed method results in reduced wait times and the ability to calculate and distribute results remotely.

The method of the present disclosure may include adjusting the synthesis process of a chemical composition based on the output at 404 (FIG. 4), such as adjusting the polymerization process, particularly, emulsion polymerization process, for preparing the polymer in the aqueous polymer composition. Parameters that can be adjusted may include, for example, surfactant types and amounts, initiator types and amounts, monomer types and sources, reaction temperatures, steam stripping parameters, or combinations thereof.

At 406, one or more predicted target product properties are generated as an output. The predicted properties may be used to determine whether prospective chemical formulation meets desired performance criteria, or whether further modifications to the formulation or article production process should be made. Target product property output may also be used to evaluate a produced product or article, allowing an operator to accept or reject a product produced from the prospective chemical formulation and/or chemical process. Modifications may include inclusion or removal of chemical components or various additives, modifying process parameters such as reaction temperatures, concentrations, reactor design, and the like. For example, predicted target product properties may include adjusting a polyurethane-forming reaction to include more or less catalyst to control target product properties such as density and hardness.

In some cases, a user may utilize an interface that enable the selection of formulation components, respective concentrations, and target product property (or properties) of interest. Once the desired criteria are input, the machine learning module provides a prediction of the target product property. The target product property generated may then be used to inform one or more of whether the prospective formulation should be further adjusted to meet the desired target product property, whether a process for generating a formulation or reaction product should be adjusted, and whether a produced product meets the expected criterion.

Computer systems disclosed herein may output one or more target product properties for a prospective formulation such as chemical formulations, material combinations, catalyst mixtures, and the like. Computer systems may include a processor and data storage, where the data storage has stored thereon computer-executable instructions that, when executed by the processor, cause the computing device to carry out functions. Computing devices may include a client device (e.g., a device actively operated by a user), a server device (e.g., a device that provides computational services to client devices), or some other type of computational platform. Some server devices can operate as client devices from time to time in order to perform particular operations, and some client devices can incorporate server features.

The processor useful in the present disclosure can be one or more of any type of computer processing element, such as a central processing unit (CPU), a co-processor (e.g., a mathematics, graphics, neural network, or encryption coprocessor), a digital signal processor (DSP), an application specific integrated circuit (ASIC), a network processor, and/or a form of integrated circuit or controller that performs processor operations.

The data storage can include one or more data storage arrays that include one or more drive array controllers configured to manage read and write access to groups of hard disk drives and/or solid-state drives.

Computing devices may be deployed to support a clustered architecture. The exact physical location, connectivity, and configuration of these computing devices can be unknown and/or unimportant to client devices. Accordingly, the computing devices can be referred to as "cloud-based" devices that can be housed at various remote data center locations, such as a cloud-based server cluster. Desirably, the computing device is a cloud-based server cluster and inputting the concentration data to the model via a web-based user interface where users can get access.

Figure 5:
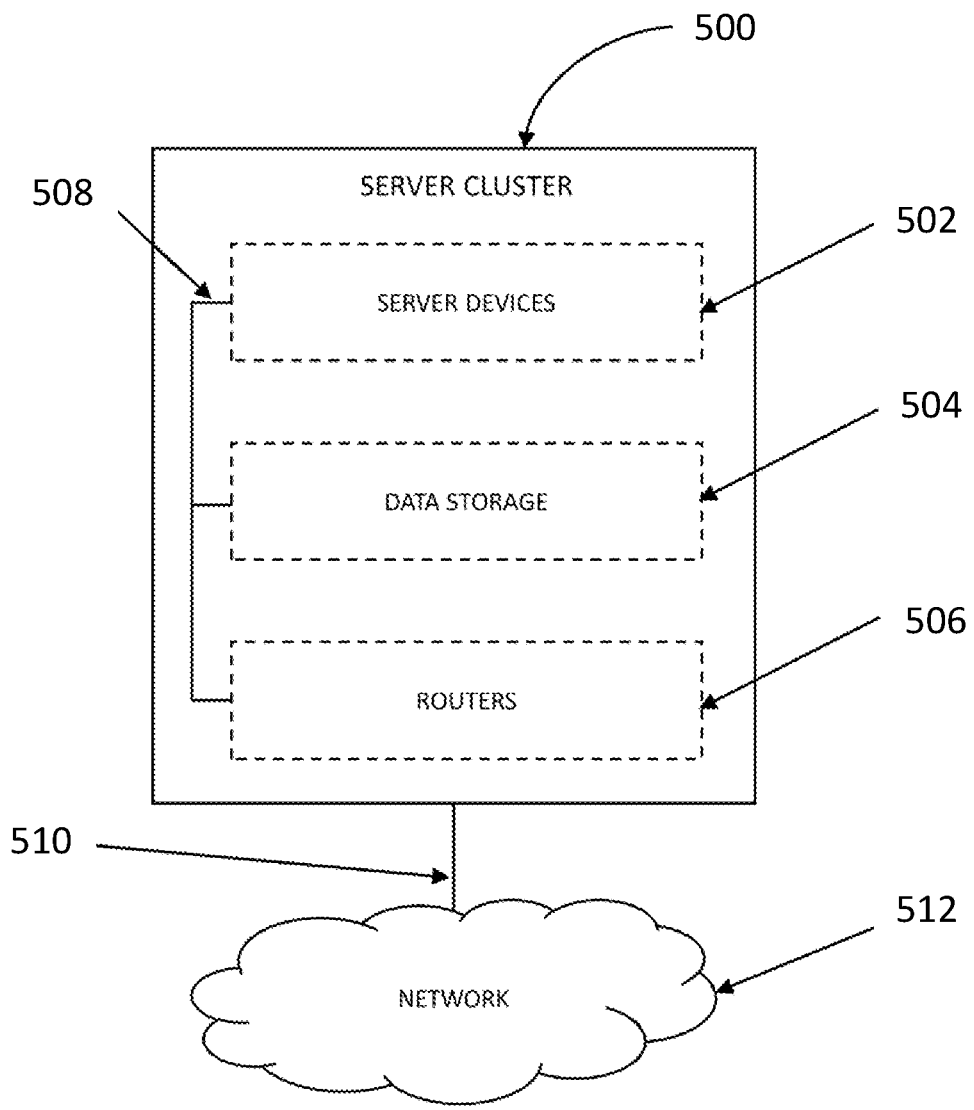
FIG. 5 illustrates a schematic drawing of a cloud-based server cluster in accordance with one example of the present disclosure.

FIG. 5 depicts a schematic drawing of a cloud-based server cluster 500 in accordance with one example of the present disclosure. Desirably, operations of a computing device can be distributed between server devices 502, data storage 504, and routers 506, all of which can be connected by local cluster network 308. The amount of server devices 502, data storage 504, and routers 506 in the server cluster 500 can depend on the computing task(s) and/or applications assigned to the server cluster 500. For example, the server devices 502 can be configured to perform various computing tasks of the computing device. Thus, computing tasks can be distributed among one or more of the server devices 502. As an example, the data storage 304 can store any form of database, such as a structured query language (SQL) database. Furthermore, any databases in the data storage 504 can be monolithic or distributed across multiple physical devices. The routers 506 can include networking equipment configured to provide internal and external communications for the server cluster 500. For example, the routers 506 can include one or more packet-switching and/or routing devices (including switches and/or gateways) configured to provide (i) network communications between the server devices 502 and the data storage 504 via the cluster network 508, and/or (ii) network communications between the server cluster 500 and other devices via the communication link 510 to the network 512. The server devices 502 can be configured to transmit data to and receive data from cluster data storage 504. Moreover, the server devices 502 can have the capability of executing various types of computerized scripting languages, such as Perl, Python, PHP Hypertext Preprocessor (PHP), Active Server Pages (ASP), or JavaScript. Computer program code written in these languages can facilitate the providing of web pages to client devices, as well as client device interaction with the web pages.

While the foregoing is directed to exemplary embodiments, other and further embodiments may be devised without departing from the basic scope thereof, and the scope thereof is determined by the claims that follow.

The invention claimed is:

1. A method of generating a hypothetical formulation library of chemical formulations, comprising generating hypothetical formulations by one or more of:
   (a) directed combinatorics, comprising:
      selecting one or more starter formulations from historical data;
      performing substitution of one or more formulation components in at least one component class for each of the starter formulations; and
      assigning concentration ratios to the formulation components within ranges established by the historical data; and
   (b) constrained randomization, comprising:
      preparing one or more template formulations comprising one or more component classes based on historical data;
      perform randomized substitution of formulation components for each of the component classes of the template formulations;
      randomly assign concentration ratios to the formulation components within ranges established by one or more constraints to produce one or more hypothetical formulations;
      create one or more descriptors for the hypothetical formulations;
      compare descriptor outputs from the hypothetical formulations with the range of descriptor outputs from the historical data; and
      remove duplicate and outlier formulations; and
   collecting the hypothetical formulations into the hypothetical formulation library.

2. The method of claim 1, further comprising validating the hypothetical formulation library using a trained machine learning module to calculate one or more predicted product properties.

3. The method of claim 2, further comprising preparing a validated formulation library based on the one or more predicted product properties.

4. The method of claim 1, wherein the chemical formulations are polyurethane formulations.

5. The method of claim 1, wherein the hypothetical formulations are generated by directed combinatorics.

6. The method of claim 1, wherein the hypothetical formulations are generated by constrained randomization.

7. The method of claim 2, wherein the predicted product properties include one or more of mechanical properties, rheology properties, density, and heat transfer properties.

8. The method of claim 1, wherein randomly assigning concentration ratios to the formulation components comprises selecting from among concentration ratios that are within 10% of the historical range for the given formulation component.

9. The method of claim 1, wherein constrained randomization comprises comparing descriptor outputs from the hypothetical formulations with the range of descriptor outputs from the historical data, and removing formulations that differ more than 10% from the descriptors in the historical data.

10. The method of claim 1, wherein the historical data comprises one or more of component variables, intercomponent reaction data, and performance properties.

* * * * *